United States Patent [19]

Moser

[11] Patent Number: 6,155,979

[45] Date of Patent: Dec. 5, 2000

[54] ULTRASONIC MEASUREMENT APPARATUS, SYSTEM AND USE OF THE SAME

[75] Inventor: Urs Moser, Zürich, Switzerland

[73] Assignee: Sulzer Innotec AG, Winterthur, Switzerland

[21] Appl. No.: 09/213,094

[22] Filed: Dec. 15, 1998

[30] Foreign Application Priority Data

Dec. 24, 1997 [EP] European Pat. Off. .............. 97811021

[51] Int. Cl.$^7$ ........................................................ A61B 8/00
[52] U.S. Cl. ............................................................... 600/445
[58] Field of Search ................................... 600/437, 441, 600/443–447, 459; 73/618, 620, 621, 625–626, 641

[56] References Cited

U.S. PATENT DOCUMENTS

| | | |
|---|---|---|
| 2,545,101 | 3/1951 | Meunier . |
| 2,768,364 | 10/1956 | Camp . |
| 4,135,406 | 1/1979 | Kretz ........................................ 73/620 |
| 4,403,509 | 9/1983 | Kretz ........................................ 73/639 |
| 5,199,437 | 4/1993 | Langberg ................................ 600/463 |

FOREIGN PATENT DOCUMENTS

| | | |
|---|---|---|
| 2077552 | 12/1981 | United Kingdom . |
| WO 87/06408 | 10/1987 | WIPO . |
| WO 96/34280 | 10/1996 | WIPO . |

*Primary Examiner*—Francis J. Jaworski
*Attorney, Agent, or Firm*—Townsend and Townsend and Crew LLP

[57] ABSTRACT

An ultrasonic measurement apparatus for an image producing ultrasonic system has a carrier body (2) which is rotatable or pivotal about an axis of rotation (A) and a plurality of transducer elements (3) which are arranged on the carrier body (2) for the emission and reception of ultrasonic signals. At least two of the transducer elements (3) are dispacedly arranged relative to one another with respect to the peripheral direction of the carrier body (2) and with respect to the axial direction determined by the axis of rotation (A).

12 Claims, 3 Drawing Sheets

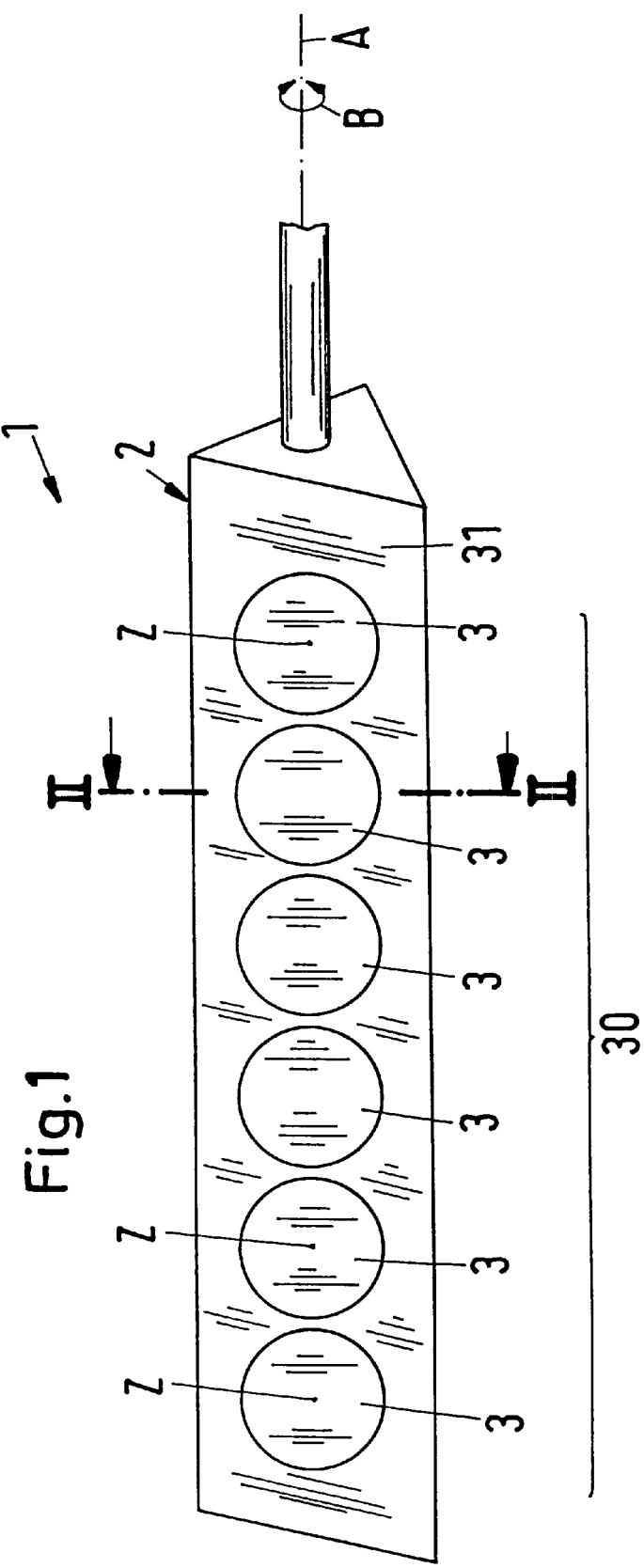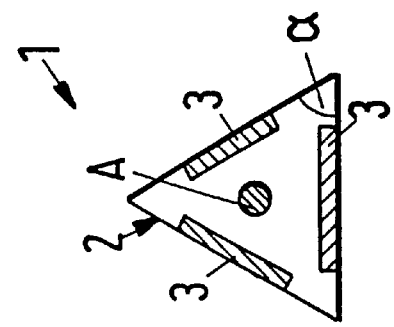

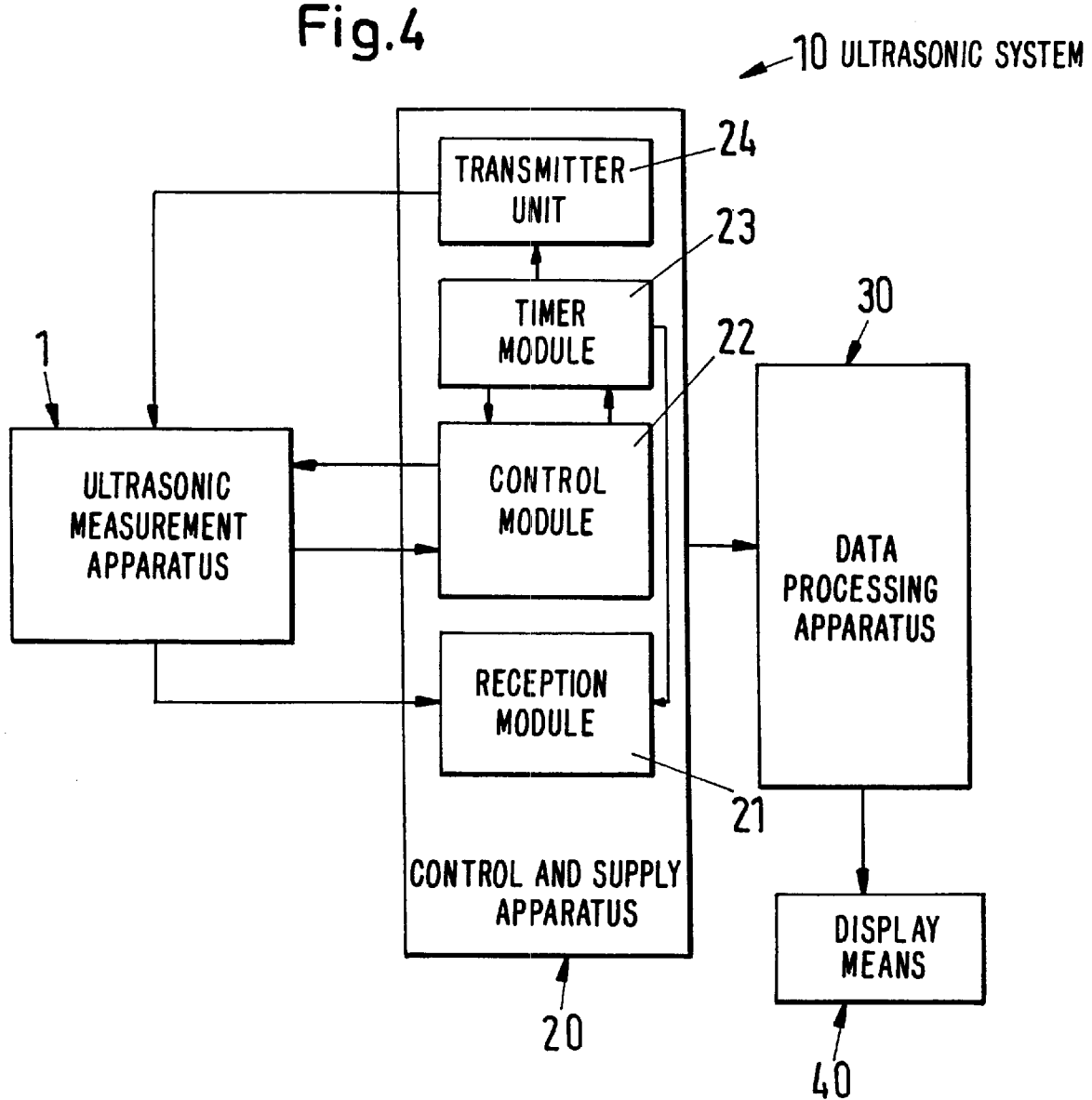

ULTRASONIC MEASUREMENT APPARATUS, SYSTEM AND USE OF THE SAME

BACKGROUND OF THE INVENTION

1. Field of the Invention

The present invention relates to an ultrasonic measurement apparatus and to the use of an apparatus or a system of this kind.

2. Description of the Prior Art

In the modern minimally invasive examination and treatment methods, image formation by means of ultrasound is accorded a special importance, among other things because it does without ionizing radiation, such as e.g. X-rays, and is thus not stressing for the patient or the doctor.

One of the numerous uses of image formation by means of ultrasound is, for example, trans-esophagal heart imaging, which is principally used for diagnostic purposes. Many of the usual ultrasonic systems today, however, produce only two dimensional images, and it is often very difficult even for specialists to analyze the three dimensional anatomy using such two dimensional images. Therefore, great efforts are being made to represent the anatomy by means of three dimensional ultrasonic images.

Ultrasonic systems which produce three dimensional images (in the following also designated as 3D-ultrasonic systems) are also already known from the prior art. In a known 3D-ultrasonic system a probe with an ultrasonic transducer is used which is pivotal with respect to two axes. Through a pivoting of the transducer about these two axes, which is usually done in an electronically controlled manner, the anatomy to be imaged, e.g. a heart chamber, is first sampled region-wise and sequentially by means of ultrasound, and a three dimensional image is then reconstructed in a data processing system from the echo signals obtained in this manner.

A substantial disadvantage of this known 3D-ultrasonic system consists in that the required sampling times for a sufficient spatial resolution of the image are relatively long. Known three dimensional systems typically require several, for example at least five, seconds for the production of a single three dimensional image. For such use as, for example, the navigation or localization of instruments required within the body, e.g. heart catheters for the ablation of stimulus lines in the heart, such long times for the image production are unsatisfactory since they are opposed to the need for a rapid and precise localization of the momentary position of the instruments in the body.

SUMMARY OF THE INVENTION

Starting from this prior art, an object of the invention is therefore to propose an ultrasonic measurement apparatus which enables a significantly more rapid production of a spatially well resolved image. In particular, the apparatus should also permit ultrasonic data to be delivered from which three dimensional images of the volume to be imaged can be reconstructed. It is furthermore an object of the invention to provide a corresponding ultrasonic system which is suitable, in particular for the rapid production of three dimensional images.

Thus, in accordance with the invention, an ultrasonic measurement apparatus for an image forming ultrasonic system is proposed, said apparatus comprising a carrier body which is rotatable or pivotal about an axis of rotation, as well as a plurality of transducer elements arranged on the carrier body for the emission and reception of ultrasonic signals. At least two of the transducer elements are arranged with a displacement relative to one another with respect to the peripheral direction of the carrier body and with respect to the axial direction determined by the axis of rotation. Through this arrangement of the transducer elements it is possible to operate a plurality of transducer elements in parallel or substantially in parallel so that a plurality of substantially parallel layers of the volume to be imaged can be sampled at the same time or almost at the same time.

This arrangement of the transducer elements consequently results in an enormous time gain from the point of view of the data acquisition required for the image production. From this, a significant reduction of the time required for the image production results. It hereby becomes possible to produce three dimensional images considerably more rapidly, e.g. in significantly less than a second. With the ultrasonic apparatus in accordance with the invention, image frequencies of three dimensional ultrasonic images of at least 10–20 images per second can be achieved in conjunction with modern data processing systems. Thus, three dimensional images can—at least approximately—be produced in real time. This is a great advantage in particular, for applications of image forming ultrasonic systems in which the localization or navigation of instruments in the body is done using ultrasonic images since a nearly continuous display of the body structures and instruments is possible.

In a preferred embodiment, the transducer elements are arranged in at least two groups which are displaced with respect to the peripheral direction of the carrier body, with the transducer elements being arranged adjacently within each group with respect to the axial direction, that is, not all at the same height in the axial direction.

Since the at least two groups of transducer elements are displacedly arranged with respect to the peripheral direction of the carrier body, a parallel sampling by the transducer elements of the first group can first be done in the operating state through pivoting or rotating the carrier body, and then a sampling by the transducer elements of the second group. Through this constructional arrangement, in particular, a better spatial resolution can be achieved, as will be explained further below.

The ultrasonic system in accordance with the invention comprises an ultrasonic measurement apparatus in accordance with the invention and thus enables the rapid production of ultrasonic images, in particular of three dimensional images. It thus enables the three dimensional, nearly continuous representation of instruments and body structures while retaining the known advantages of image production by means of ultrasound.

A preferred use of the ultrasonic system in accordance with the invention or of the ultrasonic measurement apparatus in accordance with the invention respectively is the representation, in particular the three dimensional representation, of parts of the human or animal body, in particular of the heart or of parts thereof.

BRIEF DESCRIPTION OF THE DRAWINGS

FIG. 1 is a schematic illustration of an exemplary embodiment of the ultrasonic measurement apparatus in accordance with the invention, FIG. 2 is a cross-sectional illustration of the exemplary embodiment along the section line II—II in FIG. 1, FIG. 3 is an opened up illustration of the exemplary embodiment of FIG. 1 or FIG. 2 respectively and FIG. 4 is a block diagram of an exemplary embodiment of the ultrasonic system in accordance with the invention.

DETAILED DESCRIPTION OF THE PREFERRED EXEMPLARY EMBODIMENTS

Figure 3:
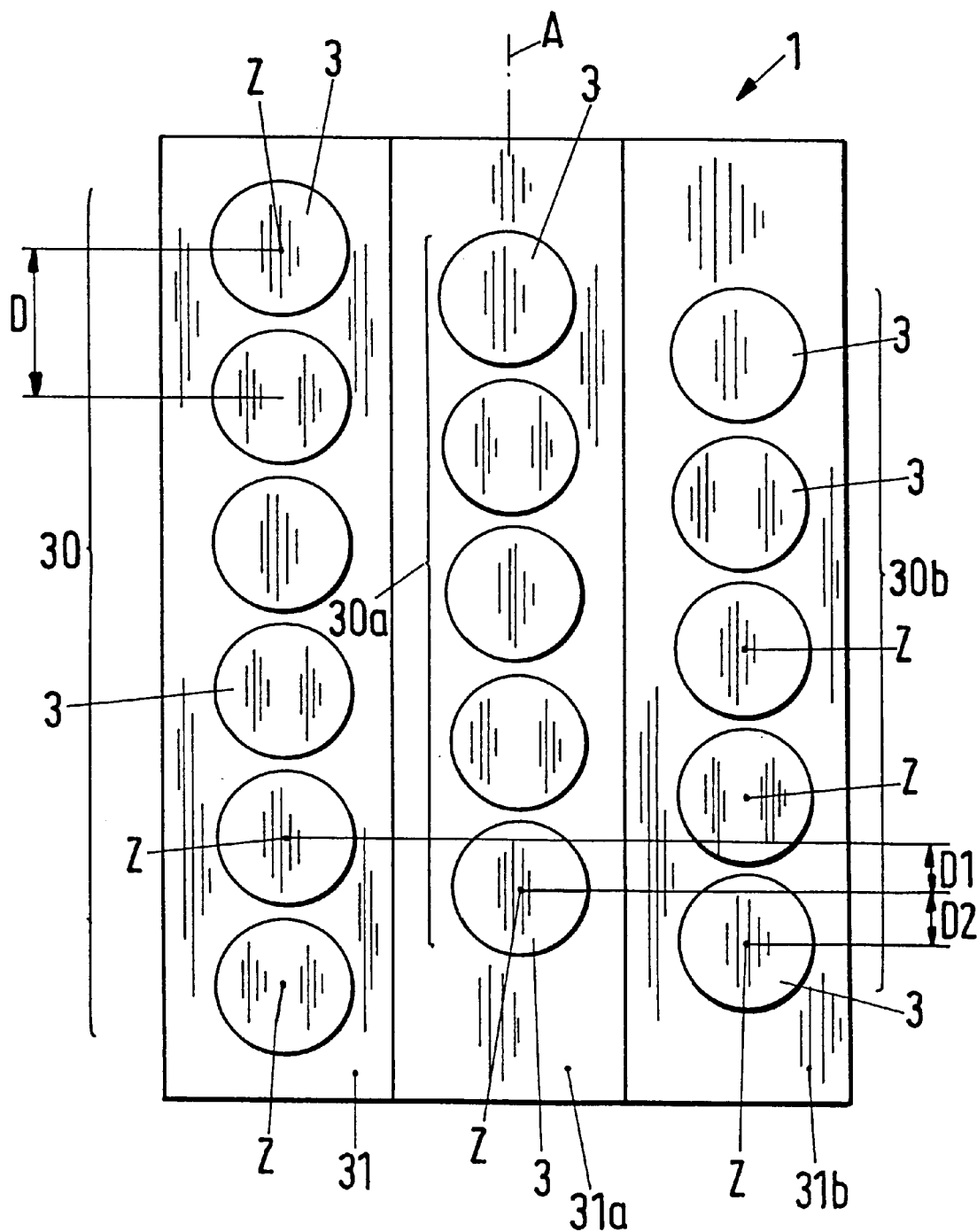

With reference to FIGS. 1–3, a preferred exemplary embodiment of the ultrasonic apparatus in accordance with the invention, which is provided in its entirety with the reference numeral 1, will first be explained in more detail. FIG. 1 shows in a schematic illustration a view, and FIG. 2 a cross-section along the section line II—II in FIG. 1 of this exemplary embodiment. FIG. 3 shows this exemplary embodiment again in an opened up illustration. It will be understood that this opened up illustration merely serves for a better understanding.

The ultrasonic measurement apparatus 1 comprises a carrier body 2 which is rotatable or pivotal about an axis of rotation A as indicated by the double arrow B in FIG. 1. A plurality of transducer elements 3 which can in each case emit and receive ultrasonic signals are arranged on the carrier body 2. Usually each transducer element 3 emits an ultrasonic signal in the form of a pulse and receives the echo signal which is reflected by the body structure to be imaged. In this exemplary embodiment the transducer elements 3 are arranged in three groups 30, 30a, 30b (see FIG. 3), with the groups 30, 30a, 30b being displaced with respect to the peripheral direction of the carrier body 2. The carrier body 2 is usually arranged in a protective sleeve or surrounded by a jacket.

In order, for example, to enable an easier introduction of the ultrasonic measurement apparatus 1 in trans-esophagal applications, the carrier body 2 can be flexibly, that is bendably executed and/or can be adapted to the anatomy.

In the exemplary embodiment described here, the carrier body 2 has; three measurement surfaces 31, 31a, 31b, which are in each case designed to be planar and in each case contain one of the groups 30 or 30a or 30b of transducer elements 3 respectively. In this the measurement surfaces 31, 31a, 31b which are adjacent are in each case arranged at an angle with respect to one another, which means that measurement surfaces 31, 31a, 31b which are adjacent intersect one another at an angle α in each case. In the exemplary embodiment described here, the three measurement surfaces 31, 31a, 31b are arranged with respect to one another in such a manner that the carrier body 2 has a triangular cross-sectional surface perpendicular to the axis of rotation A as is illustrated in FIG. 2.

Within each group 30 or 30a or 30b, respectively, the transducer elements 3 belonging to this group 30, 30a, 30b are arranged adjacently with respect to the axial direction. The axial direction is determined by the axis of rotation A, which means that the axial direction is understood to be the direction of the axis of rotation A. For constructional reasons the transducer elements 3 within each group 30, 30a, 30b are preferably arranged linearly. In this, the centers Z of the transducer elements 3 which belong to the same group 30 or 30a or 30b lie on a straight line which extends parallel to the axis of rotation A.

In the preferred exemplary embodiment in accordance with FIGS. 1–3 the transducer elements 3 are arranged in such a manner that the centers Z of the transducer elements 3 of the one group, e.g. 30, are displaced in the axial direction with respect to the centers Z of the other or of another group 30a or 30b. This arrangement can be seen best in FIG. 3. The centers Z of two directly adjacent transducer elements 3 of the same group, e.g. of the group 30 (designated in the following as the first group 30), have an axial distance D with respect to one another. The transducer elements 3 of the next group 30a in the peripheral direction (designated in the following as the second group 30a), are arranged in such a manner that their centers Z are in each case displaced in the axial direction by an amount D1 with respect to the centers Z of the transducer elements 3 of the first group 30. The transducer elements 3 of the group 30b, which is designated in the following as the third group, are arranged in such a manner that their centers Z are in each case displaced in the axial direction by an amount D2 with respect to the centers Z of the transducer elements 3 of the second group 30a. The function of this arrangement will be explained further below in connection with the description of the operating state of the ultrasonic measurement apparatus 1.

It is particularly preferred for the axial displacement D1 or D2 respectively between the centers Z of the corresponding transducer elements 3 of adjacent groups 30, 30a, 30b to be substantially equal to the quotient of the axial distance D of the centers Z of two adjacent transducer elements 3 of the same group 30 or 30a or 30b and the number of measurement surfaces 31, 31a, 31b or the number of groups 30, 30a, 30b respectively. Thus, in the exemplary embodiment explained here, preferably D1=D2=D/3, which means that the centers Z of the transducer elements of the second group 30a are in each case displaced in the axial direction with respect to the centers Z of the transducer elements 3 of the first group 30 by one third of the distance D. Analogously, the centers Z of the transducer elements 3 of the third group 30b are in each case displaced in the axial direction with respect to the corresponding centers Z of the transducer elements 3 of the second group 30a by one third of the distance D.

All ultrasonic transducers which are known per se or commercially available are suitable as transducer elements 3, for example those with single piece piezoelectric crystals. Transducer elements 3 are also suitable which have a plurality of emitter/receiver surfaces, for example in the form of concentric rings. The transducer elements 3 can fall be designed in the same manner, or different transducer elements 3 can also be used.

In the operating state, which means for the taking of ultrasonic images, the carrier body 2 of the ultrasonic measurement apparatus 1 is preferably rotated about its axis of rotation A. Depending on the concrete embodiment of the apparatus, however, it is also possible in principle to carry out a pivotal movement about the axis of rotation A instead of the rotation.

During the rotation the three groups 30, 30a, 30b of transducer elements 3 successively pass the body structure to be imaged. In this, the transducer elements 3, controlled by a control system, emit ultrasonic pulses and receive as a result the echo signal reflected by the body structure. Through the special arrangement of the transducer elements 3 in groups 30, 30a, 30b, different planes of the structure to be imaged which are substantially parallel can be sampled at the same time with ultrasound in this situation. For this, the transducer elements 3 which belong to the same group 30, 30a, 30b are in each case operated simultaneously and in parallel. The transducer elements 3 which belong to the same group 30, 30a, 30b thus produce a plurality of ultrasonic pulses which propagate substantially parallel to one another. Through this, as many different parallel planes of the structure to be imaged are sampled at the same time by a group of transducer elements 3 as there are transducer elements 3 in the corresponding group 30, 30a, 30b. Through this parallel sampling of a plurality of planes the time required for the data acquisition can be quite considerably shortened so that a three dimensional image production can take place at least approximately in real time.

Depending on the special arrangement of the transducer elements 3 with respect to the axial direction it is also possible to operate the transducer elements 3 belonging to one croup 30, 30a, 30b not exactly parallel in the sense of simultaneously, but rather substantially in parallel, by which it is meant that a time interval can lie between the activation (emission of the ultrasonic pulse) of two transducer elements 3, which is, however, significantly shorter than the travel time which an ultrasonic signal from the transducer element 3 requires in order to arrive at the structure to be imaged and from there to arrive back again at the same transducer element 3 as an echo signal. This means that two transducer elements are designated as "operated substantially in parallel" when the second transducer element is activated to emit an ultrasonic pulse before the first transducer element receives the signal which it emitted as an echo signal. A significant time gain for the measurement of the ultrasonic data also results in this "substantially parallel" operation in comparison with the serial sampling. The substantially parallel operation is advantageous in particular when, for example, the transducer elements 3 of one group, in deviation from the illustration in FIG. 3, do not all have the same position with respect to the peripheral direction of the carrier body 2, but are also displaced with respect to one another in the peripheral direction within a group.

The axial displacement of the different groups 30, 30a, 30b relative to one another (see FIG. 3) is particularly advantageous with regard to the spatial resolution which can be achieved, as will be explained in more detail in the following. In the operation of the exemplary embodiment illustrated in FIGS. 1–3, it may be assumed without a restriction of generality that the first group 30 is rotated past the structure to be imaged first. In this the six associated transducer elements 3 sample six different substantially parallel planes of the structure to be imaged. On further rotation of the carrier body 2, the second group 30a passes the structure to be imaged in turn and in so doing samples five further substantially parallel planes of the body structure with its five transducer elements 3, with these planes lying between the planes sampled by the first group 30 as a result of the axial displacement of the transducer elements 3. Finally, the third group 30b passes the structure to be imaged and in so doing likewise samples five parallel planes of the body structure with its five transducer elements 3, with these planes lying between the planes sampled by the second and the first group 30 and 30a respectively. The structure to be imaged is thereby sampled in a total of sixteen different, substantially parallel planes during one rotation of the carrier body 2. The data thus collected are converted into an image format, in particular into a three dimensional image format, in a data processing unit. In this, e.g. the information concerning the first dimension of the structure to be imaged is won from the sampling of a plane which is caused by the mechanical rotation of the carrier body 2, the information concerning the second dimension from the signals coming from the different transducer elements 3 and the information concerning the third dimension from the travel time of the echo signals. For the image reconstruction, data processing and image reconstruction procedures which are known per se from image production can be used.

The axial displacement of the individual groups 30, 30a, 30b relative to one another is admittedly particularly advantageous as a result of the increase in the spatial resolution ability, but embodiments of the ultrasonic measurement apparatus in accordance with the invention are also possible without this axial displacement. In this, for example, the different groups can always sample the same planes of the structure to be imaged so that the different planes are sampled a plurality of times per rotation of the carrier body. In this way the redundancy of the measured ultrasonic data can be increased, or it is possible to collect data for a plurality of images during one rotation of the carrier body 2.

One ultrasonic image is preferably produced per rotation of the carrier body 2 so that the rotation frequency of the carrier body 2 is equal to the image frequency. In combination with modern, rapid data processing units for example 10–20 three dimensional ultrasonic images can be produced per second, i.e. the carrier body 2 rotates at a frequency of 10–20 rotations per second. This enables an approximately continuous three dimensional representation of the body structure to be imaged, which is of great advantage in particular with regard to the localization and navigation of instruments in the body.

It is evident that numerous variations with respect to the concrete embodiment of the ultrasonic measurement apparatus 1 in accordance with the invention are possible, of which only a few shall be named here in a non-exhaustive listing.

For example, the carrier body 2 can have only two or else more than three groups 30, 30a, 30b of transducer elements 3. Thus, the carrier body can, in a manner analogous to that described above, have more than three measurement surfaces 31, 31a, 31b, of which each has a group of transducer elements 3 in each case. Furthermore, the individual measurement surfaces 31, 31a, 31b can also be curved in execution. It is also possible to design the carrier body 2 substantially cylindrically and to distribute the individual transducer elements or groups of transducer elements respectively over the jacket surface of the cylinder. Furthermore, instead of the arrangement of transducer elements 3 of a group 30, 30a, 30b on a straight line parallel to the axis of rotation A which is shown in FIGS. 1 and 3, other arrangements of the transducer elements 3 within a group can also be realized. Thus, the transducer elements 3 of a group or, respectively, their centers Z can, for example, lie on a curved line, or on a straight line which does not lie parallel to the axis of rotation A, or on a zigzag line.

In particular, if the carrier body 2 is designed cylindrically, the individual transducer elements 3 can be arranged on the jacket surface of the carrier body 2 in such a manner that their centers Z lie on a helical line. The substantially parallel operation explained above is suitable for this arrangement. The individual transducer elements can also be distributedly arranged over the jacket surface of the carrier body 2 without a special geometrical arrangement.

The number of transducer elements 3 or groups of transducer elements 3, respectively, and the number of transducer elements 3 in a group is determined, depending on the use, by the extent of the structure to be imaged in the direction of the axis of rotation A and by the desired spatial resolution ability. In this, the spatial resolution can be increased as described above in that the different transducer elements 3 or groups of transducer elements 3 respectively are displacedly arranged in the axial direction with respect to one another. This has the advantage that the spatial resolution in the direction of the axis of rotation is not limited by the number or the axial distance of the transducer elements 3 in a group respectively, but rather by the total number of transducer elements 3 which sample different planes. Therefore, the individual transducer elements 3 can be designed relatively large, for example, with a diameter of up to one centimeter (effective aperture) without concessions in the spatial resolution ability being necessary. Such relatively large transducer elements 3 are advantageous, in particular, for reasons of sonic physics.

The transmission of the signals between the transducer elements 3, which rotate in the operating state, and the usually stationary ultrasonic system can, for example, be done via brush contacts such as brush rings or other suitable coupling means, e.g. contact-less couplers such as optoelectronic, electromagnetic or inductive couplers.

In FIG. 4 essential parts of an exemplary embodiment of an ultrasonic system in accordance with the invention for image production, in particular for the production of three dimensional images, is illustrated in a schematic block diagram. The ultrasonic system is designated in its entirety by the reference numeral 10. It comprises an ultrasonic measurement apparatus 1 in accordance with the invention, a control and supply apparatus 20 for the ultrasonic measurement apparatus 1 and a data processing apparatus 30 which measures the signals delivered by the ultrasonic measurement apparatus 1 and processes them in such a manner that they can be represented as an image. The three dimensional representation can, for example, be done by a suitable display means 40 such as a monitor, a cathode ray tube in connection with 3D-eyeglasses where appropriate or a so-called head mounted display (HMD). The signal or data flow is indicated symbolically by the arrows in FIG. 4. The control and supply apparatus 20 comprises a control module 22 which is in connection with the ultrasonic measurement apparatus 1 and non-illustrated drive means for the rotation of the carrier body 2. These drive means can be part of the ultrasonic measurement apparatus 1 or else provided outside the latter. The control module 22 can furthermore be designed in such a manner that it supplies and controls non-illustrated positioning means for the measurement of the position of the ultrasonic measurement apparatus. Furthermore, the control and supply apparatus 20 comprises a timer module 23 which can communicate with the control module 22 and which together with the latter excites the individual transducer elements 3 via a transmitter unit 24 in such a manner that, on the one hand, the corresponding transducer elements 3 are in each case activated to the emission of ultrasonic pulses at the correct time during the rotation of the carrier body 2 and that, on the other hand, in each case a plurality of transducer elements 3, in particular the transducer elements 3 belonging to the same group, are operated in parallel or substantially in parallel. The ultrasonic echo signals which are received by the transducer elements 3 after their reflection at the structure to be imaged are supplied to a reception module 21 where a preprocessing of the measured data, e.g. amplification and/or filtering, takes place. The data are then supplied to the data processing apparatus 30 which digitalizes these data and converts them by means of procedures for the two or three dimensional image formation which are known per se into a format which permits a three dimensional display. The reception module 21 and the data processing apparatus 30 are likewise in contact with the timer module 23 in order to enable a correct spatial and temporal association of the data.

Furthermore, a user interface which is not shown in FIG. 4 is provided for the operation of the ultrasonic system 10.

The ultrasonic measurement apparatus 1 in accordance with the invention and the ultrasonic system 10 in accordance with the invention, respectively, are suitable in particular for the image formation of parts of the human or animal body within the framework of diagnosis and treatment procedures. In this, the ultrasonic measurement apparatus 1 is, as is generally known and usual, surrounded by a protective sleeve and is placed in the vicinity of the body structure to be imaged. Depending on the use, the ultrasonic measurement apparatus 1 can be placed either outside the body or inside it.

As a result of the enormously rapid, at least approximately continuous three dimensional image formation the subjects of the invention are suitable in particular, for uses in which instruments must be localized or navigated in the body. In this, it can be advantageous to provide the instruments with an ultrasonic marker which is controlled by the ultrasonic system 10.

The apparatus 1 in accordance with the invention or the system 10 in accordance with the invention, respectively, is particularly suitable for uses in heart diagnostics and surgery. In this, the heart imaging is preferably done transesophagally, which means that the ultrasonic measurement apparatus 1 is introduced into the esophagus and is operated there for the purpose of image production as described above. It thus enables a continuous three dimensional view into the beating heart and thereby a more precise and rapid localization and manipulation of instruments such as, for example, heart catheters in ablation treatments or the electrode positioning for heart pacemakers.

In cardiology, in particular, the ultrasonic measurement apparatus 1 in accordance with the invention or the ultrasonic system in accordance with the invention, respectively, is suitable for numerous further uses as a result of the ability to produce three dimensional images of instruments and body structures at the same time at least approximately in real time, for example: echographic determination of the beat volume, three dimensional movement analysis of the myocardium (e.g. after a heart attack), implantation and monitoring of the function of heart flap prostheses (which are biological and invisible to X-rays) navigation in minimally invasive heart surgery.

What is claimed is:

1. An ultrasonic transducer assembly for an image producing ultrasonic system comprising a carrier body for being rotated or pivoted about an axis of rotation defining an axial direction, said carrier body having at least a first and a second group of transducer elements for scanning a structure by emission and reception of ultrasonic signals, said first and second group of transducer elements being displaced with respect to a circumferential direction of the carrier body, the transducer elements within each of said first and said second group being located on the carrier body at different positions with respect to the axial direction such that upon rotating or pivoting the carrier body the first group of transducer elements scans a first set of planes of a structure and the second group of transducer elements scans a second set of planes of the structure, with the planes of the second set lying between the planes of the first set.

2. An assembly in accordance with claim 1 wherein the transducer elements within each group are located on a line extending in the axial direction.

3. An assembly in accordance with claim 1 wherein the transducer elements are located such that the centers of the transducer elements of the first group are displaced with respect to the axial direction relative to the centers of the transducer elements of the second group.

4. An assembly in accordance with claim 1 wherein the carrier body has a third group of transducer elements that are displaced relative to the first and the second group with respect to the circumferential direction of the carrier body, wherein the transducer elements are located such that the centers of the transducer elements of the third group are displaced with respect to the axial direction relative to the centers of the transducer elements of the first and the second group.

5. An assembly in accordance with claim 1 wherein the carrier body includes a plurality of measurement surfaces that each contain one of the groups of transducer elements.

6. An assembly in accordance with claim 1 wherein adjacent measurement surfaces in each case are arranged at an angle with respect to one another.

7. An assembly in accordance with claim 1 wherein the transducer elements are arranged in such a manner that the centers of the transducer elements of one group are displaced in an axial direction relative to the centers of the transducer elements of the other group by an amount that is substantially equal to the quotient of the axial distance of the centers of two adjacent transducer elements of the same group and the number of measurement surfaces.

8. An ultrasonic system for image production comprising an ultrasonic transducer assembly for the emission and reception of ultrasonic signals, a control and supply apparatus for the ultrasonic measurement apparatus and a data processing unit that captures the signals delivered by the ultrasonic measurement apparatus and processes them in such a manner that they may be represented as an image, the ultrasonic transducer assembly comprising:

a carrier body for being rotated or pivoted about an axis of rotation defining an axial direction, said carrier body having at least a first and a second group of transducer elements for scanning a structure by emission and reception of ultrasonic signals, said first and second group of transducer elements being displaced with respect to a circumferential direction of the carrier body, the transducer elements within each of said first and said second group being located on the carrier body at different positions with respect to the axial direction such that upon rotating or pivoting the carrier body the first group of transducer elements scans a first set of planes of a structure and the second group of transducer elements scans a second set of planes of the structure, with the planes of the second set lying between the planes of the first set.

9. A system in accordance with claim 8 wherein the control and supply apparatus comprises means that are executed in such a manner that in each case a plurality of transducer elements may be operated at least substantially in parallel.

10. A system in accordance with claim 9 wherein the plurality of transducer elements belong to the same group.

11. A method for scanning a structure by ultrasonic signals with an ultrasonic transducer assembly having a carrier body for being rotated or pivoted about an axis of rotation defining an axial direction, said carrier body having at least a first and a second group of transducer elements being displaced with respect to a circumferential direction of the carrier body, the transducer elements within each of said first and said second group being located on the carrier body at different positions with respect to the axial direction, the method comprising the steps of:

placing the ultrasonic transducer assembly in the vicinity of the structure to be scanned;

rotating or pivoting the carrier body such that the first group and the second group of transducer elements passes the structure;

scanning at least substantially in parallel a first set of planes of the structure by the first group of transducer elements; and scanning at least substantially in parallel a second set of planes of the structure by the second group of transducer elements, with the planes of the second set lying between the planes of the first set.

12. A method for trans-esophageally scanning a heart by ultrasonic signals with an ultrasonic transducer assembly having a carrier body for being rotated or pivoted about an axis of rotation defining an axial direction, said carrier body having at least a first and a second group of transducer elements being displaced with respect to a circumferential direction of the carrier body, the transducer elements within each of said first and said second group being located on the carrier body at different positions with respect to the axial direction, the method comprising the steps of:

introducing the ultrasonic transducer assembly into the esophagus;

placing the ultrasonic transducer assembly in the vicinity of the heart to be scanned;

rotating or pivoting the carrier body such that the first group and the second group of transducer elements passes the heart;

scanning at least substantially in parallel a first set of planes of the heart by the first group of transducer elements; and scanning at least substantially in parallel a second set of planes of the heart by the second group of transducer elements, with the planes of the second set lying between the planes of the first set.

* * * * *